United States Patent [19]

Martel et al.

[11] Patent Number: 4,554,361
[45] Date of Patent: Nov. 19, 1985

[54] PROCESS FOR THE PREPARATION OF A BICYCLIC LACTONE THROUGH A SULFONATED DERIVATIVE

[75] Inventors: Jacques Martel, Bondy; Jean Tessier, Vincennes; Jean-Pierre Demoute, Montreuil-sous-Bois, all of France

[73] Assignee: Roussel Uclaf, Paris, France

[21] Appl. No.: 517,794

[22] Filed: Jul. 27, 1983

Related U.S. Application Data

[63] Continuation of Ser. No. 359,294, Mar. 18, 1982, abandoned, Continuation-in-part of Ser. No. 173,402, Jul. 29, 1980, Pat. No. 4,331,605.

[30] Foreign Application Priority Data

Aug. 10, 1979 [FR] France .............................. 79 20477

[51] Int. Cl.$^4$ .............................................. C07D 307/77
[52] U.S. Cl. ..................................... 549/302; 549/304; 549/305
[58] Field of Search ...................... 549/302, 304, 305

[56] References Cited

U.S. PATENT DOCUMENTS

| 3,723,469 | 3/1973 | Martel | 562/506 |
| 3,950,363 | 4/1976 | Bundy | 424/285 |
| 4,014,918 | 3/1977 | Martel | 562/401 |
| 4,221,796 | 9/1980 | Wade et al. | 546/121 |

OTHER PUBLICATIONS

Wagner et al., Synthetic Organic Chemistry, John Wiley & Sons, Inc., N.Y., 1953.

Primary Examiner—Jane T. Fan
Attorney, Agent, or Firm—Charles A. Muserlian

[57] ABSTRACT

A novel process for the preparation of sulfonic acid esters containing a lactonic ring comprising compounds in the trans form in the 4- and 5-positions having (4SR,5RS), (4S,5R) or (4R,5S) configuration of the formula

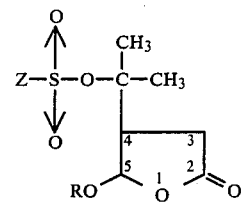

wherein Z is selected from the group consisting of alkyl of 1 to 4 carbon atoms and cycloalkyl and monocyclic aryl optionally substituted with at least one member of the group consisting of alkyl of 1 to 4 carbon atoms, alkoxy of 1 to 4 carbon atoms, halogen and nitro and R is organic residue of an optionally chiral alcohol of the formula ROH and a process using the compounds of formula I to prepare compounds of (1RS, 4RS, 5SR), (1S, 4S, 5R) or (1R, 4R, 5S) configuration of the formula

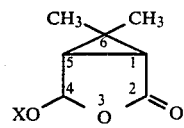

wherein X is selected from the group consisting of hydrogen and R useful for the preparation of insecticidally active esters.

11 Claims, No Drawings

PROCESS FOR THE PREPARATION OF A BICYCLIC LACTONE THROUGH A SULFONATED DERIVATIVE

PRIOR APPLICATION

This application is a continuation of U.S. patent application Ser. No. 359,294 filed Mar. 18, 1982, now abandoned which in turn is a continuation-in-part application of our copending, commonly assigned U.S. patent application Ser. No. 173,402 filed July 29, 1980, now U.S. Pat. No. 4,331,605.

STATE OF THE ART

An article relevant to the subject matter of the invention is J. Org. Chem., Vol. 39, No. 1, p. 106–108.

OBJECTS OF THE INVENTION

It is an object of the invention to provide a process for the preparation of compounds of formula I with a trans form in the 4- and 5-positions and having the configuration (4SR,5RS), (4S,5R) or (4R,5S).

It is another object of the invention to provide a novel process for the preparation of compounds of formula V having a (1RS, 4RS, 5SR), (1S,4S,5R) or (1R,4S,5S) configuration.

These and other objects and advantages of the invention will become obvious from the following detailed description.

THE INVENTION

The novel process of the invention for the preparation of compounds in the trans form in the 4- and 5-positions having (4SR,5RS), (4S,5R) or (4R,5S) configuration of the formula

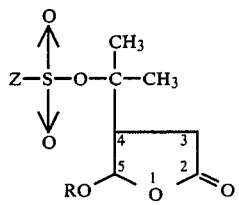

I wherein Z is selected from the group consisting of alkyl of 1 to 4 carbon atoms and cycloalkyl and monocyclic aryl optionally substituted with at least one member of the group consisting of alkyl of 1 to 4 carbon atoms, alkoxy of 1 to 4 carbon atoms, halogen and nitro and R is organic residue of an optionally chiral alcohol of the formula ROH comprises reacting a compound with the trans form in the 4- or 5-positions of the formula

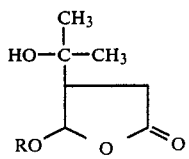

II wherein R has the above definition and when ROH is an achiral alcohol it has a (4SR,5RS) configuration and when ROH is a chiral alcohol it has a (4S,5R) or (4R,5S) configuration with a compound of the formula

III wherein Z has the above definition, n is 1 or 2 and the wavy line represents one or 2 semipolar bonds attaching the oxygen and sulfur atoms depending on whether n is 1 or 2 to obtain when n is 1 a compound with a trans form in the 4- and 5-positions of the formula

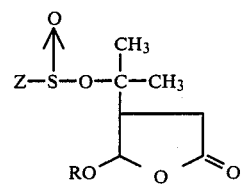

IV and reacting the latter with an oxidizing agent to obtain the corresponding compound of formula I with the trans form in the 4- and 5-positions and the (4SR,5RS) configuration if ROH is an achiral alcohol or the (4S,5R) or (4R,5S) configuration if ROH is a chiral alcohol or when n is 2, to obtain a compound of formula I with the (4SR,5RS) configuration if ROH is an achiral alcohol or the (4S, 5R) or (4R,5S) configuration if ROH is a chiral alcohol.

The use of a sulfinyl chloride (n=1) leads to the formation of a sulfinate intermediate of formula IV and this reaction is preferably effected in the presence of a tertiary base and in a solvent selected from the group consisting of aromatic hydrocarbons and halogenated hydrocarbons. Examples of suitable tertiary bases are pyridine, triethylamine, tripropylamine, triphenylamine, 2-methyl-4-ethyl-pyridine, 3-ethyl-4-methyl-pyridine and 2,4,6-trimethyl-pyridine. Preferably, the reaction is effected in methylene chloride in the presence of pyridine.

The oxidation of the sulfinate of formula IV may be effected with potassium permanganate, hydrogen peroxide, peracetic acid or p-nitroperbenzoic acid and the oxidation is preferably effected in at least one solvent selected from the group consisting of halogenated hydrocarbons, aromatic hydrocarbons, acetic acid, acetone, alkanols and water.

The use of a sulfonyl chloride (n=2) leads to the formation of the corresponding compound of formula I and the reaction is preferably effected in the presence of triethylamine in a solvent selected from the group consisting of halogenated hydrocarbons and aromatic hydrocarbons, especially benzene.

The compounds of the invention are compounds in the trans form in the 4- and 5-positions having (4SR,5RS), (4S,5R) or (4R,5S) configuration of the formula

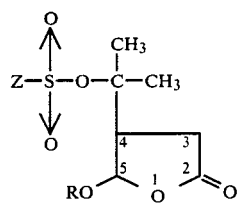

I wherein Z is selected from the group consisting of alkyl of 1 to 4 carbon atoms and cycloalkyl of 3 to 6 carbon atoms and monocyclic aryl optionally substituted with at least one member of the group consisting of alkyl of 1 to 4 carbon atoms, alkoxy of 1 to 4 carbon atoms, halogen and nitro and R is organic residue of an optionally chiral alcohol of the formula ROH.

Examples of substituents for Z are alkyl of 1 to 4 carbon atoms such as methyl, ethyl, propyl, isopropyl, n-butyl, tert.-butyl and sec.-butyl optionally substituted especially with halogen and optionally substituted monocyclic aryl such as phenyl, phenyl substituted with alkyl of 1 to 4 carbon atoms such as methyl, ethyl, propyl, isopropyl and linear or branched butyl phenyl substituted with alkoxy of 1 to 4 carbon atoms such as methoxy, ethoxy, propoxy, isopropoxy and linear or branched butoxy, phenyl substituted with halogen such as iodine, bromine, chlorine or fluorine and nitrophenyl and cycloalkyl such as cyclopropyl, cyclobutyl, cyclopentyl and cyclohexyl optionally substituted with fluorine, chlorine, bromine and —NO$_2$.

Examples of the organic radical of the chiral alcohol R—OH are

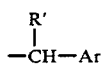

wherein R' is alkyl of 1 to 8 carbon atoms and Ar is an aryl group such as

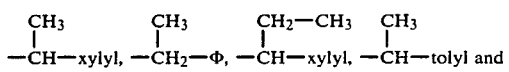

—CH$_2$—CH$_3$  R'
|  |
—CH—tolyl;  —CH—R" wherein R' and R" are alkyl of 1 to 8 carbon atoms such as —CH—CH$_2$—CH$_3$,
                        |
                        CH$_3$

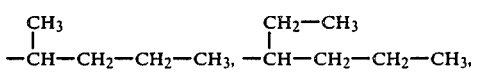

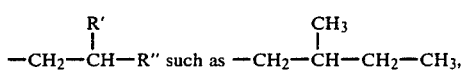

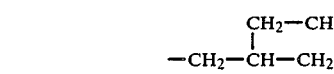

unsymmetrical butyl and pentyls; unsymmetrical cycloaliphatic groups of 4 to 10 carbon atoms such as

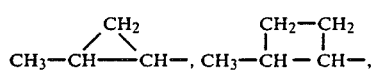

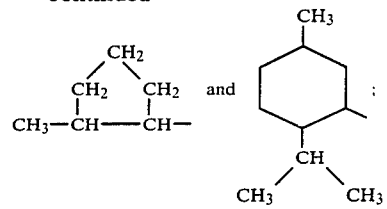

and unsymmetrical aralkyl groups of 8 to 15 carbon atoms such as

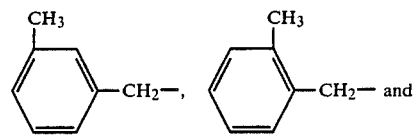

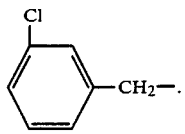

Examples of organic radicals of the non-chiral alcohols R—OH are linear or branched alkyl optionally interrupted with at least one heteroatom selected from the group consisting of oxygen, sulfur and nitrogen and optionally substituted with fluorine, chlorine, bromine and/or nitro such as methyl, ethyl, isopropyl, n-propyl, branched or linear butyl and pentyl; and optionally substituted aralkyl of 7 to 15 carbon atoms such as

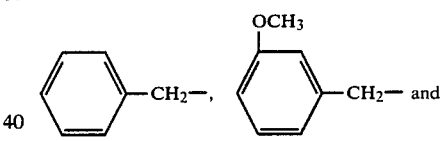

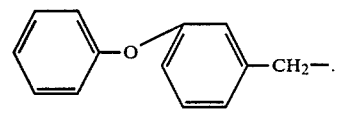

The novel process of the invention also includes the preparation of compounds of the configuration (1R,4RS,5SR) or (1S,4S,5R) or (1R,4R,5S) and having the formula

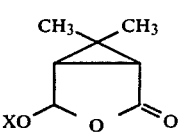

V wherein X is selected from the group consisting of hydrogen and R of an optionally chiral alcohol of the formula R—OH comprising reacting a compound of formula I with a basic agent to effect cyclization with retention of the configuration of the 4- and 5-carbon atoms to obtain a compound of formula V with (1RS,4RS,5SR) configuration when the compound of formula I has (4SR,5RS) configuration or a compound of formula V with (1S,4S,5R) configuration when the compound of formula I has (4R,5S) configuration or a compound of formula V with (1R,4R,5S) configuration when the compound of formula I has (4S,5R) configuration and optionally hydrolyzing the latter when X is R in an acid media to obtain the compound of formula V with the same configuration wherein X is hydrogen.

The basic agent to effect the cyclization is preferably an alkali metal hydroxide and this reaction is preferably effected by the phase transfer catalysis method. In a preferred mode, the cyclization is effected in methylene chloride with sodium hydroxide in the presence of triethylbenzyl ammonium chloride as catalyst and water. The hydrolysis when X is R may be effected by known methods.

The starting compounds of formula II where R is derived from an achiral alcohol may be prepared as described in commonly assigned U.S. patent application Ser. No. 153,338 filed May 27, 1980 by reacting a compound of the formula

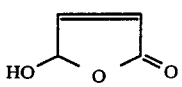
VI with an achiral alcohol of the formula R—OH to obtain a compound of the formula

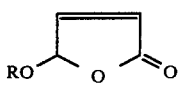
VII and reacting the latter with isopropanol in the presence of a free radical promoter. An example of the process is shown in the following specific examples.

When the compounds of formula II are optically active due to the 4- and 5-carbon atoms, they may be prepared by reacting a racemate of the compound of formula VI (R,S) with a chiral alcohol of the formula R—OH to obtain a compound of the formula

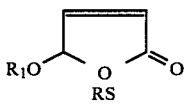
VIII and separating the two diastereoisomers by physical methods to obtain the R isomer $VIII_A$ or the S isomer $VIII_B$ and reacting one of the isomers with isopropanol in the presence of a free radical promoter to obtain a compound of formula II with the (4S,5R) or (4R,5S) configuration, respectively. The preparation of the compounds of formula $VIII_A$ and $VIII_B$ is shown in the specific examples and is further described in commonly assigned U.S. patent application Ser. No. 170,093 filed July 18, 1980.

In the method to obtain the resolved compounds of formulae $VIII_A$ and $VIII_B$, 1-menthol or (1R,2S,5R) 2-isopropyl-5-methyl-cyclobutyl-1-ol is the preferred resolution agent and the etherification of 1-menthol and (5RS) 5-hydroxy-2,5-dihydrofuran-2-one in an acid media leads by asymmetric induction to a mixture of the compounds of formulae $VIII_A$ and $VIII_B$ richer in the R form than the S form.

One part of (5R)(—)-5-[(1R,2S,5R)-2-isopropyl-5-methyl-cyclohexyloxyl-(5H)-furan-2-one is insoluble in benzene. Another heating of the mother liquors in an acid media leads to a new equilibrium between the (R) and (S) isomers and it is possible to recover another amount of the (R) form by insolubization. After 3 or 4 successive operations, an elevated yield of the (R) isomer is obtained.

The process of the invention permits in 2 or 3 reaction steps starting from compounds of formula II which are readily available, an economical stereospecific synthesis of the compounds of formula V and especially (1R,4R,5S)(—)6,6-dimethyl-4-hydroxy-3-oxabicyclo(3,1,0)hexan-2-one or (1S,4S,5R)(+)6,6-dimethyl-4-hydroxy-3-oxabicyclo(3,1,0)hexan-2-one.

The process of the invention has an unexpected character since the preparation of sulfonates of tertiary alcohols, which are difficult to realize with fragile alcohols such as the compounds of formula II, is effected in sufficiently high yields due to the type of reaction used in the process. The ultimate synthesis step involving cyclization to form the compounds of formula V had the risk of elimination reactions with the formation of a double bond or opening of the lactone ring. Due to the mild conditions of the process of the invention, secondary reactions are avoided and the final cyclization is effected in very good yields.

The compounds of formula V and especially those wherein X is hydrogen are described in French Pat. No. 1,580,474 and are useful for the preparation of a plurality of cyclopropane carboxylic acids with different substituents whose esters are known to be very active insecticides.

In the following examples there are described several preferred embodiments to illustrate the invention. However, it should be understood that the invention is not intended to be limited to the specific embodiments.

EXAMPLE 1

Trans dl 4-(2-methylsulfonyloxy-isopropyl)-5-[(3-phenoxy-phenyl)-methoxy]-tetrahydrofuran-2-one Step A: 5-(3-phenoxyphenyl)-methoxy-2-(5H)-furanone A stirred mixture of 12 g of 5-hydroxy-2-(5H)-furanone, 250 ml of benzene, 25 g of m-phenoxy-benzyl alcohol and 200 mg of p-toluene sulfonic acid was distilled to remove benzene while replacing it with an equal amount of dry benzene 4 times and after 2 hours, the mixture was cooled to room temperature and was washed with a saturated aqueous sodium bicarbonate solution and then with water. The mixture was dried and evaporated to dryness under reduced pressure to obtain 39.7 g of oil residue. The latter was chromatographed over silica gel and was eluted with a 9-1 benzene-ethyl acetate mixture to obtain 24.9 g of 5-(3-phenoxyphenyl)-methoxy-2-(5H)-furanone.

NMR Spectrum (CDCl$_3$): Peaks at 7.3–7.4 ppm (4-hydrogens of furanone); at 6.18–6.32 ppm (3-hydrogens of furanone); at 6.03 ppm (5-hydrogen of furanone); at 4.58–4.76 ppm and 4.85–5.12 ppm (hydrogens of methoxy); at 6.92 to 7.5 ppm (aromatic ring).

Step B: Trans dl 4-(2-hydroxy-isopropyl)-5-[(3-phenoxyphenyl)-methoxy]-tetrahydrofuran-2-one 300 mg of benzoyl peroxide were regularly added over 90 minutes in 25 mg portions under an inert atmosphere to a refluxing mixture of 3.5 g of the product of Step A in 100 ml of isopropanol and the mixture was then evaporated to dryness under reduced pressure at 40°–50° C. The residue was chromatographed over silica gel and was eluted with an 8-2 benzene-ethyl acetate mixture to obtain 3.7 g of product which was crystallized from isopropyl ether to obtain trans dl 4-(2-hydroxy-isopropyl)-5-[(3-phenoxyphenyl)-methoxy]-tetrahydrofuran-2-one in the form of white crystals melting at 50°-55° C.

Analysis: $C_{20}H_{22}O_5$; molecular weight=342.59, Calculated: %C 70.16 %H 6.4, Found: 69.9, 6.5.

NMR Spectrum (CDCl$_3$): Peaks at 1.18 and 1.21 ppm (hydrogens of methyls); at 2.16 and 2.75 ppm (3- and 4-hydrogens of cyclopentyl); at 4.48–4.35 ppm and 4.8–5 ppm (hydrogens of benzyl methylene); at 5.53–5.58 ppm (5-hydrogens of cyclopentyl); at 6.83 to 7.55 ppm (hydrogens of aromatic ring); at 1.5 ppm (hydrogen of OH).

Step C: Trans dl 4-(2-methylsulfonyloxy-isopropyl-5-[(3-phenoxyphenyl)-methoxy]-tetrahydrofuran-2-one 1.4 ml of triethylamine was added at 5° C. to a mixture of 1.712 g of the product of Step B in 17 ml of benzene and then a solution of 0.78 ml of methane sulfonyl chloride in 6 ml of benzene was slowly added thereto at 5° C. The mixture was stirred at 5° C. for 15 minutes and then N hydrochloric acid solution was added thereto. The decanted organic phase was washed with water, dried and evaporated to dryness to obtain 3 g of raw trans dl 4-(2-methylsulfonyloxy-isopropyl-5-[(3-phenoxyphenyl)-methoxy]-tetrahydrofuran-2-one which was usable as is.

IR Spectrum (chloroform): Absorption at 1786 cm$^{-1}$ (carbonyl of γ-lactone); at 1338 and 1172 cm$^{-1}$ (SO$_2$).

NMR Spectrum (CDCl$_3$): Peaks at 1.57–1.60 ppm (hydrogens of methyls on carbon γ to oxygen of sulfonyl); at 2.58 ppm (3- and 4-hydrogens of furanone); at 2.86 ppm (hydrogens of methyl of methansulfonyl); at 4.45–4.63 ppm and 4.73–4.92 ppm (hydrogens of methylene γ to phenoxyphenyl, quadruplet at 4.68 ppm J=11 Hz); at 5.5 ppm (4-hydrogen of furanone); at 6.83–7.5 ppm (hydrogens of aromatic ring).

EXAMPLE 2

Trans dl 4-(2-methyl-sulfonyloxy-isopropyl)-5-[(3-phenoxyphenyl)-methoxy]-tetrahydrofuran-2-one Step A: Trans dl 4-(2-methyl-sulfinyloxy-isopropyl)-5-[(3-phenoxyphenyl)-methoxy]-tetrahydrofuran-2-one 3.08 g of trans dl 4-(2-hydroxy-isopropyl)-5-[(3-phenoxyphenyl)-methoxy]-furan-2-one were added to a mixture of 3 ml of pyridine and 10 ml of methylene chloride and after cooling the mixture to 0° C., a solution of 0.89 g of methane sulfinyl chloride in 5 ml of methylene chloride was progressively added thereto. The mixture was stirred at 0° C. for one hour and was then washed with N hydrochloric acid and then with water. The mixture was dried and evaporated to dryness under reduced pressure to obtain 3.7 g of raw trans dl 4-(2-methylsulfinyloxy-isopropyl)-5-[(3-phenoxyphenyl)-methoxy]-tetrahydrofuran-2-one.

IR Spectrum (chloroform): Absorption at 1781 cm$^{-1}$ (carbonyl of γ-lactone); at 1585 and 1489 cm$^{-1}$ (3-phenoxyphenyl); at 1395 cm$^{-1}$ (methyls on carbon γ- to oxygen of sulfinate); at 1119 cm$^{-1}$ (S→O); at 694 cm$^{-1}$ (phenyl ring).

NMR Spectrum (CDCl$_3$): Peaks at 1.40–1.42–1.50 ppm (hydrogens of methyls on carbon γ- to oxygen of sulfinyl); at 2.17–2.92 ppm (3- and 4-hydrogens of furanone); at 2.55–2.58 ppm (methyl of methanesulfinyl); at 4.48–4.7 ppm and 4.78–4.98 ppm (methylene γ- to 3-phenoxyphenyl quadruplet at 284 nm J=12.5 Hz); at 5.38–5.42 ppm and 5.51–5.55 ppm (5-hydrogen of furanone-qudruplet at 5.63 ppm J=2.5 Hz).

Step B: Trans dl 4-(2-methylsulfonyloxy-isopropyl)-5-[(3-phenoxyphenyl)-methoxy]-tetrahydrofuran-2-one 0.430 g of p-nitro-perbenzoic acid were added to a mixture of 0.627 g of the product of Step A in 70 ml of methylene chloride and the mixture was stirred for 100 minutes at 20° C. and was then filtered. The filtrate was washed with water, dried and filtered to obtain a solution of trans dl 4-(2-methylsulfonyloxy-isopropyl)-5-[(3-phenoxyphenyl)-methoxy]-tetrahydrofura-2-one in methylene chloride. A sample of the solution was concentrated to dryness and analysis of the product showed it had the same physical characteristics of the product of Example 1.

EXAMPLE 3

Trans dl 4-(2-ethyl-sulfonyloxy-isopropyl)-5-[(3-phenoxyphenyl)-methoxy]-tetrahydrofuran-2-one Step A: Trans dl 4-(2-ethyl-sulfinyloxy-isopropyl)-5-[(3-phenoxyphenyl)-methoxy]-tetrahydrofuran-2-one A solution of 1 g of ethane sulfonyl chloride in 5 ml of methylene chloride was progressively added at −10° C. to a mixture of 2 g of trans dl 4-(2-hydroxy-isopropyl)-5-[(3-phenoxyphenyl)-methoxy]-tetrahydrofuran-2-one, 1 ml of pyridine and 10 ml of methylene chloride and the mixture then stood at 0° C. for 2 hours and was poured into a dilute aqueous hydrochloric acid solution. The organic phase was washed with water, dried and evaporated to dryness unde reduced pressure to obtain 2.57 g of trans dl 4-(2-ethyl-sulfinyloxy-isopropyl)-5-[(3-phenoxyphenyl)-methoxy]-tetrahydrofuran-2-one.

IR Spectrum (chloroform): Absorption at 1783 cm$^{-1}$ (lactonic carbonyl); at 1113 cm$^{-1}$ (S→O).

NMR Spectrum (CDCl$_3$): Peaks at 1.07–1.18–1.3 ppm (hydrogens of CH$_3$ of ethyl of ethylsulfinyl); at 1.4–1.45–1.52 ppm (hydrogens of methyls of carbon γ- to oxygen of sulfinyl); at 2.52–2.92 ppm (methylene of ethyl of ethylsulfinyl); at 4.48–4.68–4.78–4.9 ppm (methylene of 5 phenylmethoxy of furanone); at 5.48–5.-52–5.62–5.66 ppm (5-hydrogen of furanone); at 6.92–7.58 ppm (aromatic ring).

Step B: Trans dl 4-(2-ethylsulfonyloxy-isopropyl)-5-[(3-phenoxyphenyl)-methoxy]-tetrahydrofuran-2-one 0.50 g of anhydrous potassium acetate was progressively added to a suspension of 0.44 g of the product of Step A in 4.5 ml of methylene chloride and then 1.6 ml of a peracetic acid solution containing 40.5% of acetic acid, 31% peracetic acid and 17.3% of hydrogen peroxide were added thereto over 2 hours. The mixture at 0° C. was slowly poured into aqueous sodium thiosulfate solution and the mixture was extracted with methylene chloride. The organic phase was washed with sodium bicarbonate solution and then with water, dried and evaporated to dryness under reduced pressure. The residue was chromatographed over silica gel and was eluted with an 8-2 benzene-ethyl acetate mixture to obtain 0.33 g of trans dl 4-(2-ethylsulfonyloxy-isopropyl)-5-[(3-phenoxyphenyl)-methoxy]-tetrahydrofuran-2-one which was saved at a low temperature in solution in a mixture of methylene chloride and benzene. The IR spectrum and NMR were identical to those of the compound of Example 1.

EXAMPLE 4

Trans dl 4-(2-ethyl-sulfonyloxy-isopropyl)-5-[(3-phenoxy-phenyl)-methoxy]-tetrahydrofuran-2-one 0.084 g of potassium permanganate was added at 0° C. to a mixture of 0.214 g of trans dl 4-(2-ethylsulfinyloxy-isopropyl)-5-[(3-phenoxyphenyl)-methoxy]-tetrahydrofuran-2-one, 4 ml of acetone, 0.3 ml of acetic acid and 2 ml of water and the mixture was stirred at 0° C. for 2 hours. A solution of 0.050 g of potassium permanganate, 1 ml of water and 1 ml of acetone was added to the mixture which was then stirred at 0° C. for 17 hours and was poured into a sodium thiosulfate solution. The mixture was extracted with methylene chloride and the organic phase was washed with sodium bicarbonate solution and then with water, dried and evaporated to dryness without heating. The residue was chromatographed over silica gel and eluted with an 8-2 benzene-ethyl acetate mixture to obtain 0.090 g of trans dl 4-(2-ethyl-sulfonyloxy-isopropyl)-5-[(3-phenoxyphenyl)-methoxy]-tetrahydrofuran-2-one whose IR and NMR spectrum were identical to the compound of Example 1.

EXAMPLE 5

Trans dl 4-(2-isopropyl-sulfonyloxy-isopropyl)-5-[(3-phenoxy-phenyl)-methoxy]-tetrahydrofuran-2-one Step A: Trans dl 4-(2-isopropyl-sulfinyloxy-isopropyl)-5-[(3-phenoxyphenyl)-methoxy]-tetrahydrofuran-2-one 3.25 g of trans dl 4-(2-hydroxy-isopropyl)-5-[(3-phenoxyphenyl)-methoxy]-tetrahydrofuran-2-one were added to a mixture of 3 ml of pyridine and 10 ml of methylene chloride and a solution of 1.2 g of isopropane sulfinyl chloride in 5 ml of methylene chloride was progressively added at 0° C. to the mixture. The mixture was stirred at 20° C. for 17 hours, was washed with hydrochloric acid, with water and evaporated to dryness under reduced pressure to obtain 4.2 g of trans dl 4-(2-isopropyl-sulfinyloxy-isopropyl)-5-[(3-phenoxyphenyl)-methoxy]-tetrahydrofuran-2-one.

IR Spectrum (CHCl$_3$): Absorption at 1780 cm$^{-1}$ ($\gamma$-lactone carbonyl); at 1583, 1486 cm$^{-1}$ (3-phenoxyphenyl); at 1392 and 1379 cm$^{-1}$ (geminal methyls); at 1110 cm$^{-1}$ (—O—S→O).

NMR Spectrum (CDCl$_3$): Peaks at 1.08–1.52 ppm (hydrogens of methyls of isopropyl); at 2.0–3.0 ppm (3- and 4-hydrogens of furanone and hydrogen on carbon $\gamma$ to sulfur atom); at 4.45–4.65 ppm and 4.75–4.95 ppm (hydrogens of methylene $\gamma$- to phenoxyphenyl-quadruplet at 282 ppm J=12 Hz); at 5.44–5.48 ppm and 5.57–5.61 ppm (5-hydrogen of furanone-quadruplet at 331.5 ppm J=2.5 Hz).

Step B: Trans dl 4-(2-isopropylsulfonyloxy-isopropyl)-5-[(3-phenoxyphenyl)-methoxy]-tetrahydrofuran-2-one 0.287 g of p-nitroperbenzoic acid (titrating 80%) was added to a mixture of 0.404 g of the product of Step A in 10 ml of methylene chloride and the mixture was stirred at 20° C. for 50 minutes and was then filtered. The filtrate was washed with aqueous sodium bicarbonate solution, then with water and evaporated to dryness under reduced pressure to obtain 0.520 g of trans dl 4-(2-isopropylsulfonyloxy-isopropyl)-5-[(3-phenoxyphenyl)-methoxy]-tetrahydrofuran-2-one.

IR Spectrum (CHCl$_3$): Absorption at 1782 cm$^{-1}$ ($\gamma$-lactone carbonyl); at 1583 and 1485 cm$^{-1}$ (3-phenoxyphenyl); at 1330 cm$^{-1}$ and 1152–1160 cm$^{-1}$ (—O—SO$_2$).

EXAMPLE 6

Trans dl 4-[2-(p-tolylsulfonyloxy)-isopropyl]-5-[(3-phenoxy-phenyl)-methoxy]-tetrahydrofuran-2-one Step A: Trans dl 4-[2-(p-tolylsulfinyloxy)-isopropyl]-5-[(3-phenoxyphenyl)-methoxy]-tetrahydrofuran-2-one 10 ml of pyridine were added at 0° C. to a mixture of 20 ml of methylene chloride, 1.5 g of trans dl 4-(2-hydroxyisopropyl)-5-[(3-phenoxyphenyl)-methoxy]-tetrahydrofuran-2-one and 0.802 g of p-tolylsulfinyl chloride and the mixture was stirred at 0° C. for 3 hours and was then poured into aqueous N hydrochloric acid solution. The mixture was extracted with benzene and the organic phase was washed with aqueous hydrochloric acid, aqueous sodium bicarbonate solution and was concentrated to dryness under reduced pressure. The residue was chromatographed over silica gel and was eluted with an 8-2 benzene-ethyl acetate mixture to obtain trans dl 4-[2-(p-tolylsulfinyloxy)-isopropyl]-5-[(3-phenoxyphenyl)-methoxy]-tetrahydrofuran-2-one.

IR Spectrum (CHCl$_3$): Absorption at 1783 cm$^{-1}$ ($\gamma$-lactone carbonyl); at 1585 and 1488 cm$^{-1}$ (3-phenoxyphenyl); at 1393 cm$^{-1}$ (geminal methyls); at 1110–1145 cm$^{-1}$ (S→O).

NMR Spectrum (CDCl$_3$): Peaks at 1.50–1.58 ppm (hydrogens of geminal methyls); at 2.38 ppm (hydrogen of methyl of p-tolyl); at 2.57–2.62 ppm (4- and 5-hydrogens of tetrahydrofuran-ring); at 4.41–5.0 ppm (hydrogens of methylene $\alpha$- to 3-phenoxyphenyl); at 5.4–5.53 ppm (hydrogen of tetrahydrofuranyl-2-stereoisomers); at 6.83–7.50 ppm (aromatic ring)1.

Step B: Trans dl 4-[2-(p-tolylysulfonyloxy)-isopropyl]-5-[(3-phenoxyphenyl)-methoxy]-tetrahydrofuran-2-one A mixture of 0.320 g of p-nitroperbenzoic acid (titrating 80%) 0.420 g of the product of Step A and 10 ml of chloroform was stirred for 3½ hours and was then cooled to −10° C. and filtered. The filtrate was concentrated under reduced pressure and was then filtered again. The filtrate was evaporated to dryness under reduced pressure to obtain trans dl 4-[2-(p-tolyl sulfonyloxy)-isopropyl]-5-[(3-phenoxyphenyl)-methoxy]-tetrahydrofuran-2-one.

IR Spectrum (CHCl$_3$): Absorption at 1783 cm$^{-1}$ ($\gamma$-lactone carbonyl); at 1350 and 1175 cm$^{-1}$ (—SO$_2$).

EXAMPLE 7

6,6-dimethyl-4-[(3-phenoxyphenyl)-methoxy]-3-oxabicyclo(3,1,0)hexan-2-one 2 ml of aqueous sodium hydroxide solution (50 g of sodium hydroxide per 100 g) were added at 20° C. to a solution of 0.30 g of trans dl 4-(2-ethylsulfonyloxy-isopropyl)-5-[(3-phenoxyphenyl)-methoxy]-tetrahydrofuran-2-one in 3 ml of methylene chloride and then 0.015 g of triethylenzyl ammonium chloride was added thereto. The mixture was stirred at 20° C. for 25 minutes and was then poured into an iced aqueous monosodium phosphate solution. The mixture was extracted with methylene chloride and the organic phase was evaporated to dryness under reduced pressure. The residue was chromatographed over silica gel and was eluted with a 7-3 petroleum ether (b.p. =35°–75° C.)-ether mixture to obtain 0.140 g of 6,6-dimethyl-4-[3-phenoxyphenyl]-methoxy]-3-oxabicyclo(3,1,0)hexan-2-one melting at 66° C.

EXAMPLE 8

(4S,5R)4-[2-methylsulfonyloxy-isopropyl]-5-[(1R, 2S, 5R)-2-isopropyl-5-methyl-cyclohexyloxy]-tetrahydrofuran-2-one Step A: (5R)(—)-[(1R, 2S, 5R)-2-isopropyl-5-methyl-cyclohexyloxy]-(5H)-furan-2-one A mixture of 32.5 g of 1-menthal, 21 g of 5-hydroxy-2,5-dihydro-furan-2-one, 0.2 g of p-toluene sulfonic acid and 300 ml of benzene was refluxed while azeotropically eliminating the water of reaction and then 4 g of 5-hydroxy-2,5-dihydrofuran-2-one were added thereto after which the mixture was refluxed for one hour and was cooled. The organic solution was washed with sodium bicarbonate solution and then with water, dried and evaporated to dryness under reduced pressure. The 51.6 g of residue were diluted with 100 ml of petroleum ether (b.p.=35°–70° C.) and the mixture stood at 0° C. for 17 hours and was vacuum filtered to obtain 15 g of (5R)(—)[(1R, 2S,5R)-2-isopropyl)-5-methyl-cyclohexyloxy]-(5H)-furan-2-one in the form of crystals melting at 76° C.

The mother liquors were evaporated to dryness and the residue was diluted with 150 ml of benzene. 200 mg of p-toluene sulfonic acid were added to the mixture which was refluxed for 3 hours and was cooled. The mixture was washed with aqueous sodium bicarbonate solution, then with water, dried and evaporated to dryness. The residue was crystallized from petroleum ether (b.p.=35°–70° C.) to obtain another 35 g of the said product melting at 76° C. The subsequent treatments of the mother liquors yielded 5.7 and 3.4 g of the product melting at 76° C. for a total yield of 34.45 g of the desired product with a specific rotation of $[\alpha]_D^{20} = -139°$ (c=1.5% in chloroform).

NMR Spectrum (CDCl$_3$): Peaks at 0.75–0.86 ppm, 0.86–1.0 ppm and 0.83–0.94 ppm (hydrogens of 6-methyl of menthyl and hydrogens of methyls of 2-isopropyl of menthyl); at 3.66 ppm (1-hydrogen of menthyl) at 6.10–6.12–6.13 ppm (5-hydrogens of furanone); at 6.16–6.18 ppm and 6.25–6.26 ppm (3-hydrogen of furanone); at 7.13–7.15 ppm and 7.21–7.23 ppm (4-hydrogen of furanone).

Step B: (4S, 5R)(—)[(1R,2S,5R)2-isopropyl-5-methyl-cyclohexyloxy]-4-(2-hydroxy-isopropyl)-tetrahydrofuran-2-one 0.125 g of calcium carbonate was added to a solution of 5 g of the product of Step A in 100 ml of isopropanol and the mixture was refluxed under an inert atmosphere for 5 minutes. 0.200 g of benzoyl peroxide were added to the mixture which was refluxed for 3½ hours and was cooled and filtered. The filtrate was evaporated to dryness under reduced pressure and the residue was stirred with water and was vacuum filtered. The residue was chromatographed over silica gel and eluted with an 8–2 benzene-ethyl acetate mixture. The product was crystallized from petroleum ether to obtain (4S,5R)(—)[(1R,2S,5R)2-isopropyl-5-methyl-cyclohexyloxy]-4-(2-hydroxy-isopropyl)-tetrahydrofuran-2-one with a specific rotation of $[\alpha]_D^{20} = -154.5° \pm 2.5°$ (c=1.5% in chloroform).

IR Spectrum (CHCl$_3$): Absorption at 3608 cm$^{-1}$ (OH); at 1777 cm$^{-1}$ ($\gamma$-lactone carbonyl)

NMR Spectrum (CDCl$_3$): Peaks at 0.73–0.85–0.82–0.93 ppm (hydrogens of methyls of 2-isopropyl of cyclohexyl); at 0.88–0.96 ppm (hydrogens of 5-methyl of cyclohexyl); at 1.22–1.28 ppm (hydrogens of methyls on carbon $\gamma$ to hydroxy); at 5.67–5.72 ppm (5-hydrogen of furanone).

Step C: (4S,5R)-4-(2-methylsulfonyloxy-isopropyl)-5-[(1R,2S,5R)2-isopropyl-5-methyl-cyclohexyloxy]-tetrahydrofuran-2-one 1.5 ml of triethylamine were added at 5° C. to a solution of 1.5 g of the product of Step B in 30 ml of benzene and then a solution of 0.8 ml of methane sulfonyl chloride in 6 ml of benzene were slowly added thereto at 5° C. The mixture was poured into iced water and the decanted organic phase was washed with aqueous monosodium phosphate solution, with aqueous sodium bicarbonate solution and then with water, dried and evaporated to dryness under reduced pressure. The (4S,5R)-4-(2-methylsulfonyloxy-isopropyl)-5-[(1R,2S,5R)2-isopropyl -5-methyl-cyclohexyloxy]-tetrahydrofuran-2-one was saved as a methylene chloride solution at 0° C.

IR Spectrum (CHCl$_3$): Absorption at 1780 cm$^{-1}$ ($\gamma$-lactone carbonyl); at 1339–1178 cm$^{-1}$ (—O—S→O).

NMR Spectrum (CDCl$_3$): Peaks at 0.73–0.75–0.83–0.95 ppm (hydrogens of methyls of 2-isopropyl of cyclohexyl); at 0.88–0.98 ppm (hydrogens of 5-methyl of cyclohexyl); at 1.65–1.72 ppm (hydrogens of methyls on carbon $\gamma$-to oxygen of sulfonyl).

EXAMPLE 9

(1R, 4R, 5S)(—)6,6-dimethyl-4-[(1R, 2S, 5R)2-isopropyl-5-methyl-cyclohexyloxy]-3-oxabicyclo(3,1,0)-hexan-2-one 5 ml of aqueous 50% sodium hydroxide solution were added at 5° C. to the methylene chloride solution of Example 8 and 0.050 g of triethylbenzylammonium chloride was added thereto at 10°–15° C. The mixture was vigorously stirred at 12° ± 2° C. for 2½ hours and was then slowly poured into an aqueous monosodium phosphate solution. The mixture was extracted with methylene chloride and the organic phase was washed with water, dried and evaporated to dryness under reduced pressure. The residue was chromatographed over silica gel and was eluted with an 8–2 petroleum ether-ether mixture to obtain 1.18 g of (1R,4R,5S)(—)6,6-dimethyl-4-[(1R, 2S, 5R)2-isopropyl-5-methyl-cyclohexyloxy]-3-oxabicyclo(3,1,0)-hexan-2-one melting at 82° C. and having a specific rotation of $[\alpha]_D^{20} = -195° \pm 2°$ (c=4% in chloroform). The product was identical to the product obtained by condensation of 1-menthol and (1R,4R,5S)(—) 6,6-dimethyl-4-hydroxy-3-oxabicyclo (3,1,0) hexan-2-one.

Analysis: C$_{17}$H$_{28}$O$_3$; molecular weight=280.42, Calculated: %C 72.81, %H 10.06, Found: 72.9, 10.0.

In a manner analogous to Example 8, 4-[2-isopropyl-sulfonyloxy-isopropyl]-5-[(3-phenoxyphenyl)-methoxy]-tetra-hydrofuran-2-one was reacted using aqueous sodium hydroxide in methylene chloride and triethylbenzylammonium chloride to obtain (1R,4R, 5S) 6,6-dimethyl-4-[(3-phenoxyphenyl)-methoxy]-3-oxabicyclo-(3,1,0)-hexan-2-one.

EXAMPLE 10

(1R,4R,5S)(—)6,6-dimethyl-4-hydroxy-3-oxabicyclo(3,1,0)hexan-2-one 8 ml of 0.5N aqueous hydrochloric acid were slowly added to a solution of 0.805 g of the product of Example 9 melting at 82° C. in 8 ml of acetone and the mixture was stirred at 20° C. for 4 hours. The aqueous phase was extracted with petroleum ether and the aqueous phase was evaporated to dryness under reduced pressure to obtain 0.360 g of (1R,4R,5S)(—)6,6-dimethyl-4-hydroxy-3-oxabicyclo(3,1,0)hexan-2-one melting at 116° C. and having a specific rotation of $[\alpha]_D^{20} = -114° \pm 1.5°$ (c=1% in dimethylformamide).

Various modifications of the products and process of the invention may be made without departing from the spirit or scope thereof and it should be understood that the invention is intended to be limited only as defined in the appended claims.

What is claimed is:

1. A process for the preparation of a compound of the configuration (1R,4RS,5SR) or (1S,4S,5R) or (1R,4R,5S) having the formula

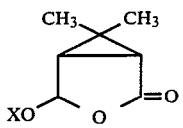

wherein X is selected from the group consisting of hydrogen and R, R is the residue of an alcohol of the formula —R—OH wherein R is selected from the group consisting of chiral

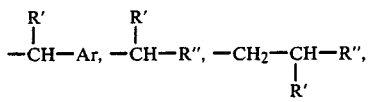

unsymmetrical cycloalkyl of 4 to 10 carbon atoms and unsymmetrical aralkyl groups of 8 to 15 carbon atoms, achiral alkyl of 1 to 5 carbon atoms, achiral alkyl of 1 to 5 carbon atoms interrupted with at least one heteroatom selected from the group consisting of —O—, —S— and —N— and achiral alkyl of 1 to 5 carbon atoms substituted with at least one member of the group consisting of fluorine, chlorine, bromine and —NO₂, aralkyl and aralkyl substituted by alkoxy or aryloxy containing 7 to 15 carbon atoms, R' and R" are alkyl of 1 to 8 carbon atoms, Ar is an aryl of 6 to 8 carbon atoms comprising (a) reacting a compound with the trans form in the 4- and 5-positions of the formula

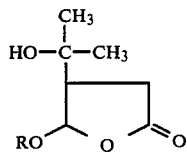

wherein R has the above definition and when R is a residue of an achiral alcohol ROH as defined above, it has a (4SR,5RS) configuration and when R is a residue of a chiral alcohol R—OH as defined above, it has a (4S,5R) or (4R,5S) configuration, with a compound of the formula

wherein Z is selected from the group consisting of alkyl of 1 to 4 carbon atoms, cycloalkyl of 3 to 6 carbon atoms and monocyclic aryl and alkyl of 1 to 4 carbon atoms, cycloalkyl of 3 to 6 carbon atoms and monocyclic aryl, all substituted with at least one member of the group consisting of alkyl of 1 to 4 carbon atoms, alkoxy of 1 to 4 carbon atoms, halogen and nitro, n is 1 or 2 and the wavy line represents one or 2 semipolar bonds attaching the oxygen and sulfur atoms depending on whether n is 1 or 2, to obtain when n is 1, a compound with a trans form in the 4- and 5-positions of the formula

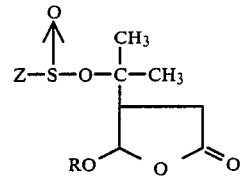

and reacting the latter with an oxidizing agent capable of oxidizing sulfoxide to sulfone to obtain the corresponding compound of the formula

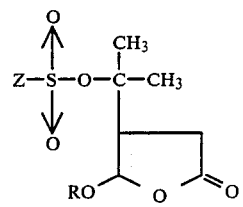

with the trans form in the 4- and 5-positions and the (4SR,5RS) configuration if R is a residue of an achiral alcohol ROH or the (4S,5R) or (4R,5S) configuration if R is a residue of a chiral alcohol R—OH or to obtain, when n is 2, the above compound of formula I, (b) reacting the compound of formula I with an alkali metal hydroxide to effect cyclization with retention of the configuration of the 4- and 5-carbon atoms, to obtain a compound of formula V with (1RS,4RS,5SR) configuration when the compound of formula I has (4SR, 5SRS) configuration, or a compound of formula V with (1S,4S,5R) configuration, when the compound of formula I has (4R,5S) configuration or a compound of formula V with (1R,4R,5S) configuration when the compound of formula I has (4S,5R) configuration and (c), if desired, hydrolyzing the compound of formula I wherein when X is R, in an acid media, to obtain the compound of formula V with the same configuration wherein X is hydrogen.

2. A process of claim 1 wherein Z is selected from the group consisting of alkyl of 1 to 4 carbon atoms, alkyl of 1 to 4 carbon atoms substituted with halogen, cycloalkyl of 3 to 6 carbon atoms, cycloalkyl of 3 to 6 carbon atoms substituted with halogen and nitro, aryl and aryl substituted with at least one member of the group consisting of alkyl of 1 to 4 carbon atoms, alkoxy of 1 to 4 carbon atoms, halogen and nitro and R is derived from a chiral alcohol and is selected from the group consisting of

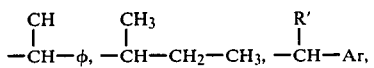

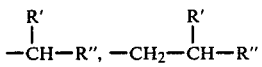

unsymmetrical cycloalkyl and unsymmetrical aralkyl, R' and R" are alkyl of 1 to 8 carbon atoms or R is derived from a non-chiral alcohol and is selected from the group consisting of alkyl of 1 to 8 carbon atoms, alkyl of 1 to 8 carbon atoms interrupted with at least one heteroatom selected from the group consisting of oxygen, nitrogen and sulfur, alkyl of 1 to 8 carbon atoms substituted with halogen and nitro and aralkyl of 7 to 15 carbon atom selected from the group consisting of

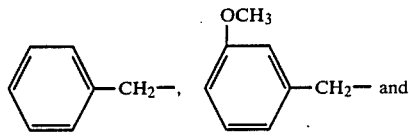

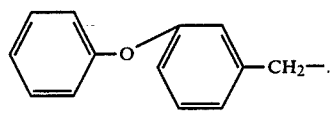

3. The process of claim 1 wherein n is 1 and the reaction with the sulfinyl chloride is effected in the presence of a tertiary base and in a solvent selected from the group consisting of halogenated hydrocarbons and aromatic hydrocarbons.

4. The process of claim 3 wherein the tertiary base is pyridine and the solvent is methylene chloride.

5. The process of claim 1 wherein the oxidizing agent is selected from the group consisting of potassium permanganate, hydrogen peroxide, peracetic acid and p-nitroperbenzoic acid.

6. The process of claim 1 wherein the reaction with the oxidizing agent is effected in at least one solvent selected from the group consisting of halogenated hydrocarbons, aromatic hydrocarbons, acetic acid, acetone, alkanols and water.

7. The process of claim 1 wherein n is 2 and the reaction with the sulfonyl chloride is effected in the presence of triethylamine and in a solvent selected from the group consisting of halogenated hydrocarbons and aromatic hydrocarbons.

8. The process of claim 1 wherein the solvent is benzene.

9. The process of claim 1 wherein R is selected from the group consisting of

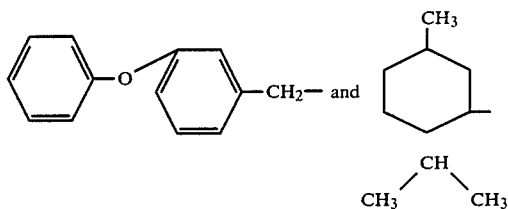

10. The process of claim 1 wherein the alkali metal hydroxide is used, according to a phase transfer catalysis method.

11. The process of claim 10 wherein the solvent is methylene chloride, the basic agent is sodium hydroxide, the catalyst is triethylbenzyl ammonium chloride and water is present.

* * * * *